United States Patent [19]
Lin

[11] Patent Number: 5,578,035
[45] Date of Patent: Nov. 26, 1996

[54] EXPANDABLE BONE MARROW CAVITY FIXATION DEVICE

[76] Inventor: Chih-I Lin, 14292 Spring Vista La., Chino Hills, Calif. 91709

[21] Appl. No.: 442,110

[22] Filed: May 16, 1995

[51] Int. Cl.⁶ .................................................. A61B 17/56
[52] U.S. Cl. .................. 606/68; 606/65; 606/67
[58] Field of Search .............................. 606/62, 64, 65, 606/66, 67, 68

[56] References Cited

U.S. PATENT DOCUMENTS

| 3,716,051 | 2/1973 | Fischer | 606/68 |
| 3,791,380 | 2/1974 | Dawidowski | 606/68 |
| 4,498,468 | 2/1985 | Hansson | 606/68 |

OTHER PUBLICATIONS

Catalog of the Vitallium; Compression Hip Screw Appliance; by Howmedica International.
Catalog of the Gamma Locking Nail; Locking Nail System; by Howmedica International.

Primary Examiner—Michael Powell Buiz
Assistant Examiner—Mark S. Leonardo
Attorney, Agent, or Firm—Bacon & Thomas

[57] ABSTRACT

An expandable bone marrow cavity fixation device comprises a hollow tubular body provided peripherally with a plurality of through holes, in each of which a diameter-adjusting element is movably disposed. An adjustment element is adjustably disposed in the hollow interior of the tubular body such that the inner end of the diameter-adjusting element is urged by the adjustment element. An urging element is rotatably disposed in the hollow interior of the tubular body such that the upper end of the adjustment element is urged by the bottom end of the urging element, and that the adjustment element can be so actuated by a rotational motion of the urging element as to force the diameter-adjusting elements to jut out of the through holes of the tubular body to bring about an increase in outer diameter of the tubular body. Located at the top of the tubular body is a pulling and fixing device fastened thereto to facilitate the pulling and the locating of the device of the present invention after the bone marrow cavity of a fractured bone is urged intensively by the outer ends of the diameter-adjusting elements. The tubular body or the adjustment element is provided with a retaining device engageable securely with a retaining element of each of the diameter-adjusting elements for preventing the diameter-adjusting elements from becoming disengaged with the through holes of the tubular body.

5 Claims, 4 Drawing Sheets

EXPANDABLE BONE MARROW CAVITY FIXATION DEVICE

FIELD OF THE INVENTION

The present invention relates generally to an orthopedic fixation device, and more particularly to a bone marrow cavity fixation device which can be stretched out as desired.

BACKGROUND OF THE INVENTION

A deformed femoral joint or a fractured trochanter may be surgically treated with various artificial hip joints or femur fixing systems, which are all disclosed in the U.S. Pat. Nos. 5,007,910; 5,041,114; 5,116,336; and 5,122,141. Such devices as mentioned above comprise a threaded rod, which is fastened onto the trochanter so as to enable the trochanter to be pulled back to join with the femur. However, such devices are defective in design in that the fractured trochanter can not be caused to position again correctly by rotating the threaded rod, and that the devices can not be adjusted diametrically.

SUMMARY OF THE INVENTION

It is therefore the primary objective of the present invention to provide an expandable bone marrow cavity fixation device with a diameter adjusting element capable of urging an inner cavity.

It is another objective of the present invention to provide an expandable bone marrow cavity fixation device comprising a hollow tubular body, a plurality of diameter-adjusting elements, an adjustment element, and an urging element and pulling back fixation means.

The hollow tubular body has a hollow interior provided with an open top. The tubular body is provided peripherally with a plurality of through holes communicating the hollow interior with the outside of the tubular body.

The diameter-adjusting elements are received in the through holes of the tubular body such that the diameter-adjusting elements can be caused to jut out. The diameter-adjusting elements are provided respectively with a holding element.

The adjustment element is received in the hollow interior of the tubular body such that the inner ends of the diameter-adjusting elements are urged by the adjustment element.

The urging element is inserted into the hollow interior of the tubular body via the open top of the hollow interior such that the bottom end of the urging element is in contact with the top end of the adjustment element, and that the adjustment element can be actuated by a rotational motion of the urging element to cause the diameter-adjusting elements to jut out of the through holes so as to bring about an increase in diameter of the tubular body.

The tubular body is further provided at the top thereof with a fixation member fastened thereto and intended to enable the tubular body to be pulled upwards.

The tubular body or the adjustment element is provided with a retaining means engageable with the holding elements of the diameter-adjusting elements for preventing the diameter-adjusting elements from becoming disengaged with the through holes in which the diameter-adjusting elements are movably disposed.

The tubular body is provided in the vicinity of an axis thereof with a hollow interior which is in turn provided in the proximity of the lower end thereof with a plurality of through holes communicating the hollow interior with the outside of the tubular body.

The lower end of the tubular body is divided into 3–10, preferably 3–6, peripheral surfaces which are provided respectively with a plurality of through holes. The through holes of the same peripheral are preferably located on the same cross-sectional surface. In addition, the angles formed by the adjoining through holes are preferably equal to one another. The peripheral surfaces are preferably corresponding in number of through hole to one another. The through holes are arranged alternately or correspondingly such that they are located on a straight line parallel to the axis of the hollow interior of the tubular body.

The diameter-adjusting elements are so shaped as to cooperate with the through holes in which the diameter-adjusting elements are movably received. It is suggested that the diameter-adjusting elements are columnar or cylindrical in shape, and that the diameter-adjusting elements are provided respectively at the outer end thereof with an arcuate surface having a considerable curvature. The diameter-adjusting elements are provided respectively with a holding element engageable with the retaining means of the tubular body or the adjustment element. If the tubular body is provided with the retaining means, the diameter-adjusting elements are preferably provided in the vicinity of the outer end thereof with the holding element. On the other hand, if the adjustment element is provided with the retaining means, the diameter-adjusting elements are preferably provided in the vicinity of the inner end thereof with the holding element. The retaining means or holding element may be similar in construction to the retaining means of the prior art.

The adjustment element may be a corrugated shaft which has various portions with different diameters or an eccentric bearing. The corrugated shaft is made up of a plurality of spherical or oval bodies which are in contact one after another. The eccentric bearing comprises an eccentric circular track, which may be replaced with an oval circular track. For simplicity, the adjustment element is preferably a corrugated shaft made up of a plurality of individual spherical bodies in contact one after another. The spherical bodies may be coupled one after another to form an integral corrugated shaft.

If the adjustment element is a corrugated shaft, it is suggested that the tubular body is provided in the outer end of the through holes thereof with the retaining means which may be a retaining hole having a diameter smaller than the diameter of the holding element. The retaining hole is formed by making the outer end of the through hole smaller. The tubular body may be provided with a casing having a plurality of retaining holes. The holding element may be a protuberance having a diameter greater than the diameter of the retaining holes.

When the eccentric bearing is employed as the adjustment element, the retaining means is preferably located on the adjustment element. In other words, the outer hole of the eccentric circular track or the oval circular track of the eccentric bearing serves as a retaining means. In the meantime, the holding element of the diameter-adjusting elements is a protuberance having a diameter greater than the inner diameter of the outer hole of the eccentric circular track or the oval circular track of the eccentric bearing. The protuberance referred to above may be an elastic body capable of springing back to its original size and shape after being squeezed and then released.

The urging element is dimensioned to fit into the hollow interior of the tubular body via the open top of the hollow interior. As the urging element is advanced or rotated, the adjustment element is actuated by an advancing motion or rotational motion of the urging element so as to cause the diameter-adjusting elements to jut out of the through holes. For example, the adjustment element is made up of a plurality of spherical bodies while the urging element is a screw engageable with a threaded open top of the hollow interior of the tubular body. The extent to which the diameter-adjusting elements are forced to jut out of the through holes depends on the degree to which the screw is advanced in the hollow interior so as to regulate the positions of the spherical bodies of the adjustment element. If the eccentric bearing is used as the adjustment element, the urging element may be columnar in shape. It is recommended that the columnar urging element is made integrally with the eccentric bearing which serves as the adjustment element.

The pulling back fixation means of the present invention is similar in construction to any prior art nut-plate-screw fixation device, such as the Vitallium® Compression Hip Screw Appliance and the Gamma Locking Nail® System sold by Howmedica Corporation of the United States.

The foregoing objectives, features, functions, and advantages of the present invention will be more readily understood upon a thoughtful deliberation of the following detailed description of the embodiments of the present invention in conjunction with the accompanying drawings.

DETAILED DESCRIPTION OF THE EMBODIMENTS

Figure 1:
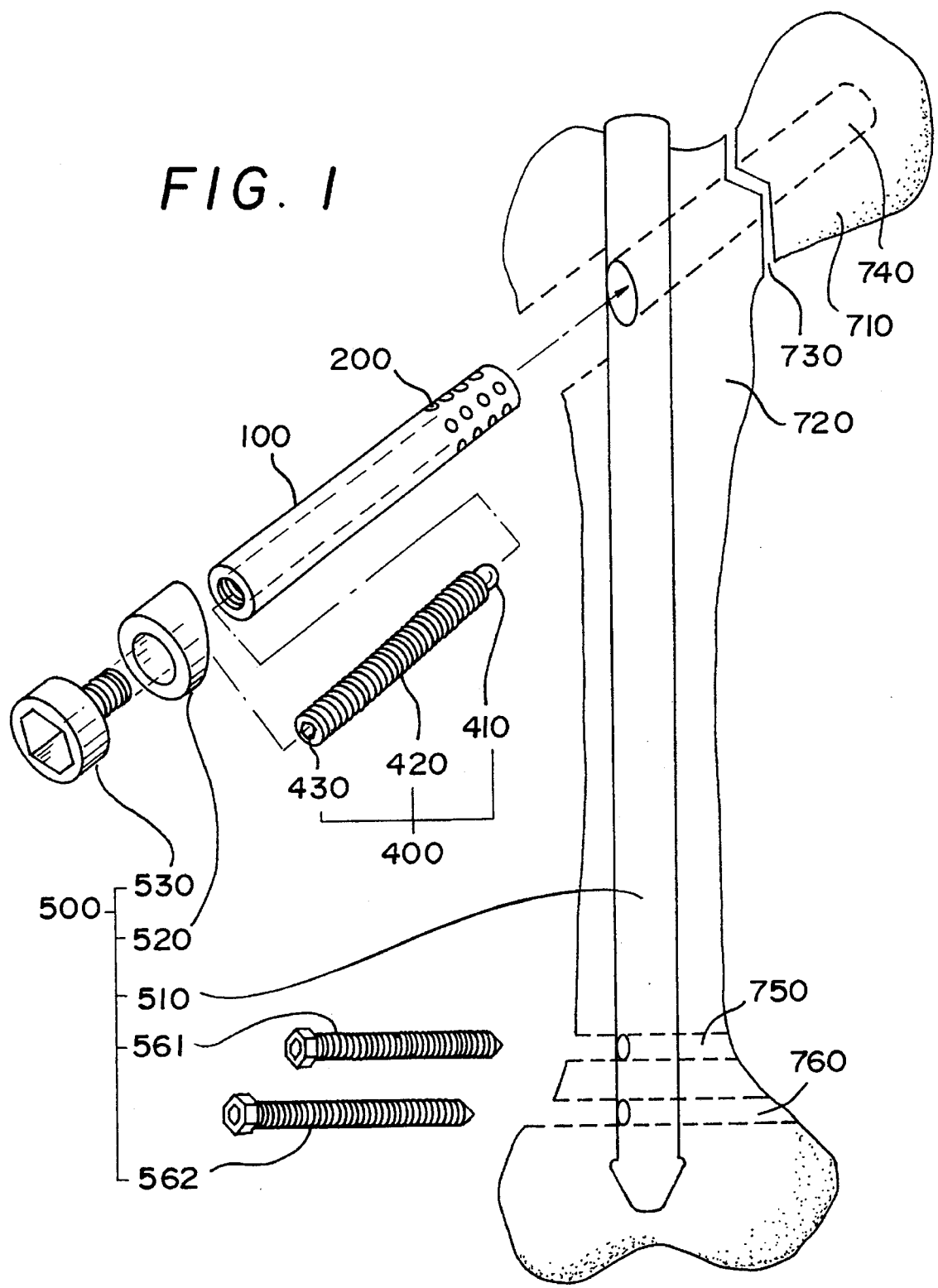
FIG. 1 shows an exploded view of a first preferred embodiment of the present invention.
Figure 2A:
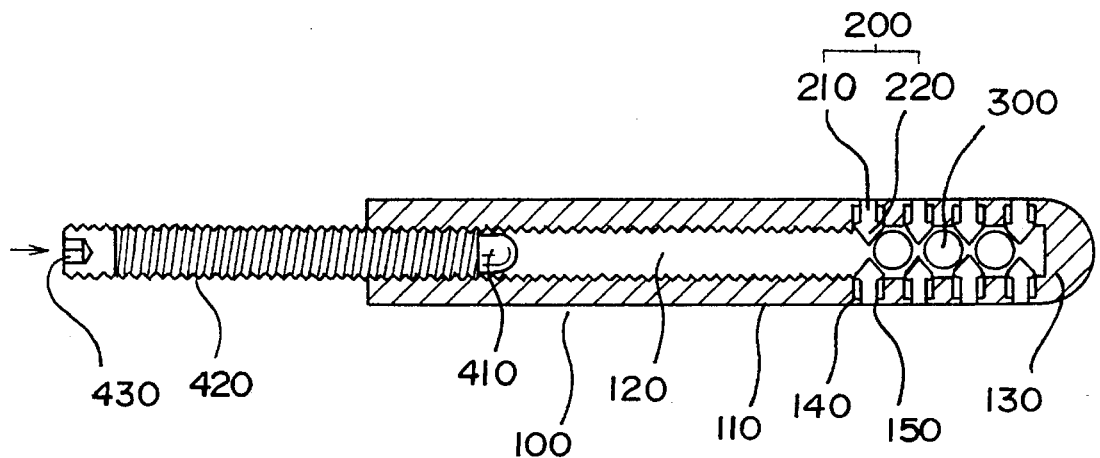
FIGS. 2a to 2b are schematic views showing the tubular body, the diameter-adjusting elements and the adjustment element of the first preferred embodiment of the present invention.
Figure 2B:
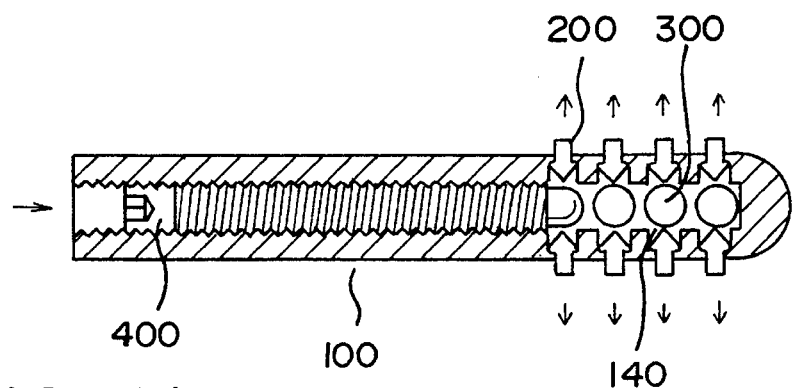
Figure 3:
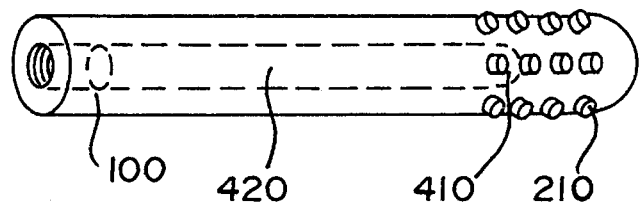
FIG. 3 is a perspective schematic view of FIG. 2b.

As shown in FIGS. 1 and 3, the first preferred embodiment of the present invention comprises a tubular body 100, a plurality of diameter-adjusting elements 200, an urging element 400, and a pulling back fixation means 500. The urging element 400 is provided with an urging end 410, a threaded portion 420, and a tool hole 430. The pulling back fixation means 500 comprises a bone marrow inner nail 510, a washer 520, a pulling back screw 530, and two fastening screws 561 and 562. The reference numerals of hip joint, femur, and the fractured area are respectively 710, 720 and 730. The fastening holes 740, 750 and 760 are made in advanced. The tubular body 100, along with the diameter-adjusting elements 200, is guided into the fastening hole 740 while the urging element 400 is inserted into the hollow interior of the tubular body 100. For more details, please refer to FIGS. 2a to 2b. The diameter-adjusting elements 200 are urged by the urging element 400 to jut out to urge intensively the bone tissue of the femur. The tubular body 100 is received in a through hole formed on the bone marrow inner nail 510 and is then fitted into the washer 520 before the pulling back screw 530 is fastened onto the top end of the tubular body 100. When the pulling back screw 530 is fastened continuously and the head of the pulling back screw 530 is urging the washer 520, the tubular body 100, along with the hip joint 740, will be pulled toward the washer 520.

As shown in FIG. 2a, the tubular body 100 comprises a wall 110, a hollow interior 120, a tail end 130, a plurality of through holes 140, and a retaining device 150. The diameter-adjusting elements 200 are provided respectively with a columnar body 210 and a holding element 220. As shown in FIG. 2a, the diameter-adjusting elements 200 are not caused to jut out of the through holes 140 of the tubular body 100. As shown in FIG. 2b, the diameter-adjusting elements 200 are caused by the adjustment element 300 to jut out of the through holes 140 of the tubular body 100 when the urging element 400 is fastened onto the tubular body 100 to actuate the adjustment element 300.

Figure 4:
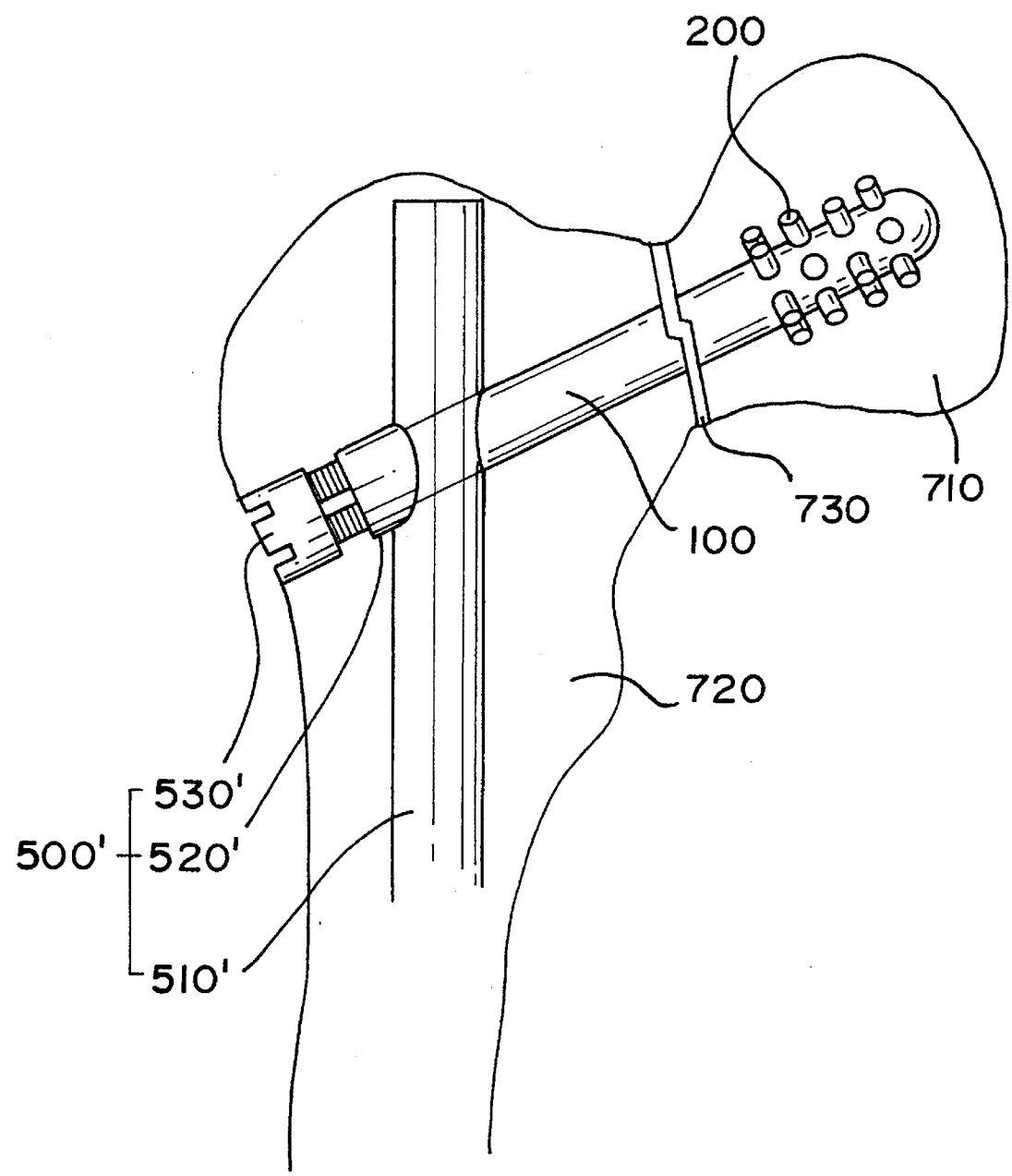
FIG. 4 shows a schematic view of a second preferred embodiment of the present invention.

As shown in FIG. 4, the second preferred embodiment of the present invention is different from the first preferred embodiment of the present invention in that the former is provided with the pulling back fixation member 500' which is in fact the pulling back fixation means of the Gamma Locking Nail® system made by the Howmedica Corporation of the United Stated. The reference numerals of 510', 520' and 530' are similar in definition to the like reference numerals without apostrophe of FIG. 1.

Figure 5A:
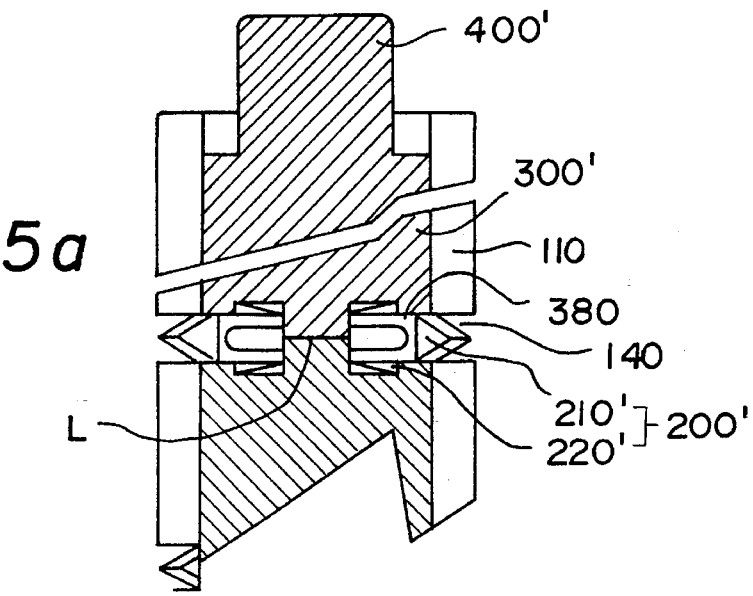
FIGS. 5a to 5e are schematic views of a third preferred embodiment of the present invention and of each component part of the present invention.
Figure 5B:
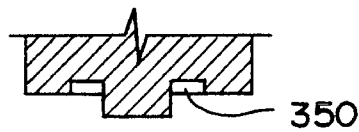
Figure 5C:
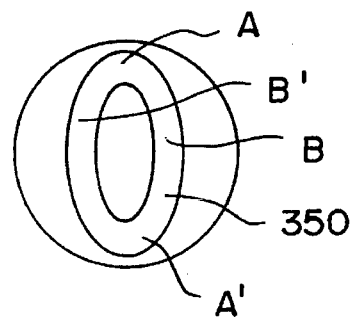
Figure 5D:
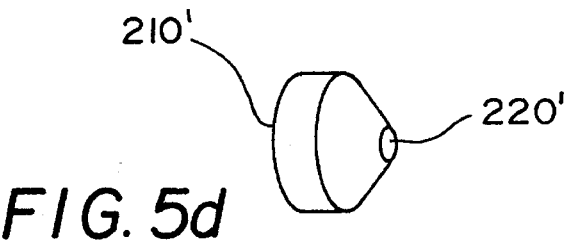
Figure 5E:
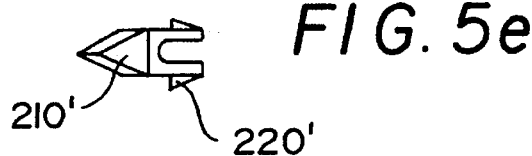

As shown in FIGS. 5e to 5f, the third preferred embodiment of the present invention comprises an eccentric bearing 300' serving as the adjustment element. The eccentric bearing 300' is provided with a retaining means 380 and is made integrally with the urging element 400' The eccentric bearing 300' is provided with an oval slot 350 while the diameter-adjusting elements 200' are provided respectively with a holding element 220'. When the urging element 400' is rotated to actuate the eccentric bearing 300 so as to cause the retaining element 220 of the diameter-adjusting elements 200' to be held by the oval slot 350 at B or B' point, the diameter-adjusting elements 200' are caused to remain entirely in the through holes 140. After the device of the present invention is properly implanted, the urging element 400' can be so rotated as to actuate the eccentric bearing 300' to retain the retaining elements 220' of the diameter-adjusting elements 200' by means of the oval slot 350 at points A and A'. As a result, the tapered outer end 210' of the diameter-adjusting elements 200' are forced to jut out of the through holes 140 of the tubular body 100 to urge intensively the bone marrow cavity of a fractured bone intended to be fixed.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

What is claimed is:

1. An expandable bone marrow cavity fixation device comprising:

a tubular body having a hollow interior provided with an open top, said tubular body provided peripherally with a plurality of through holes communicating said hollow interior with the outside of said tubular body;

a plurality of diameter-adjusting elements received movably in said through holes of said tubular body and provided respectively with a holding element;

at least one adjustment element received adjustably in said hollow interior of said tubular body such that an inner end of each of said diameter-adjusting elements is urged by said at least one adjustment element;

an urging element inserted into said hollow interior of said tubular body via said open top of said hollow interior such that an upper end of said at least one adjustment element is urged by a bottom end of said urging element, and that said at least one adjustment element can be actuated by a rotational motion of said urging element so as to cause an outer end of each of said diameter-adjusting elements to jut out of said through hole of said tubular body to bring about an increase in outer diameter of said tubular body; and a pulling back fixation means fastened to said open top of said tubular body for connecting said tubular body to a bone marrow inner nail and pulling said tubular body in the direction toward said bone marrow inner nail;

wherein one of said tubular body and said at least one adjustment element is provided with a retaining means engageable securely with said holding element of each of said diameter-adjusting elements for preventing said diameter-adjusting elements from becoming disengaged with said through holes of said tubular body.

2. The expandable bone marrow cavity fixation device as defined in claim 1, wherein said at least one adjustment element is composed of a plurality of spherical bodies.

3. The expandable bone marrow cavity fixation device as defined in claim 1, wherein said open top of said hollow interior of said tubular body is a threaded hole; and wherein said urging element is a screw engageable with said threaded hole.

4. The expandable bone marrow cavity fixation device as defined in claim 1, wherein said at least one adjustment element is an eccentric bearing.

5. The expandable bone marrow cavity fixation device as defined in claim 4, wherein said urging element is of a columnar construction and is made integrally with said at least one adjustment element.

\* \* \* \* \*